US009662104B1

United States Patent
Nobles et al.

(10) Patent No.: US 9,662,104 B1
(45) Date of Patent: May 30, 2017

(54) THROW AND CATCH SUTURING DEVICE WITH A CURVED NEEDLE

(71) Applicant: HeartStitch, Inc., Fountain Valley, CA (US)

(72) Inventors: Anthony Nobles, Fountain Valley, CA (US); Melanie Hempel, Schwarzenberg (DE)

(73) Assignee: HEARTSTITCH, INC., Fountain Valley, CA (US)

( * ) Notice: Subject to any disclaimer, the term of this patent is extended or adjusted under 35 U.S.C. 154(b) by 0 days.

(21) Appl. No.: 15/132,552

(22) Filed: Apr. 19, 2016

Related U.S. Application Data

(60) Provisional application No. 62/267,771, filed on Dec. 15, 2015.

(51) Int. Cl.
| | | |
|---|---|---|
| *A61B 17/04* | (2006.01) | |
| *A61B 17/06* | (2006.01) | |
| *A61B 17/00* | (2006.01) | |

(52) U.S. Cl.
CPC .... *A61B 17/0469* (2013.01); *A61B 17/06066* (2013.01); *A61B 2017/00367* (2013.01); *A61B 2017/047* (2013.01); *A61B 2017/06071* (2013.01)

(58) Field of Classification Search
CPC .............. A61B 17/06; A61B 17/06004; A61B 17/06066; A61B 17/0482; A61B 17/0469; A61B 2017/047; A61B 2017/06042; A61B 2017/06071; A61B 2017/0608
See application file for complete search history.

(56) References Cited

U.S. PATENT DOCUMENTS

| | | |
|---|---|---|
| 5,608,962 A | 3/1997 | Colligan et al. |
| 5,709,693 A | 1/1998 | Taylor |
| 6,346,111 B1 | 2/2002 | Gordon et al. |
| 6,755,843 B2 | 6/2004 | Chung et al. |
| 8,100,922 B2 | 1/2012 | Griffith |
| 8,123,764 B2 | 2/2012 | Meade et al. |
| 8,246,638 B2 | 8/2012 | Perez-Cruet et al. |
| 2009/0259105 A1 | 10/2009 | Miyano et al. |
| 2014/0148825 A1 | 5/2014 | Nobles et al. |
| 2014/0214038 A1 | 7/2014 | Sholev et al. |
| 2015/0126815 A1 | 5/2015 | Nobles et al. |
| 2015/0351750 A1* | 12/2015 | Chin .................. A61B 17/0469 606/145 |

FOREIGN PATENT DOCUMENTS

WO     2008/147555 A3     12/2008

\* cited by examiner

*Primary Examiner* — Jonathan Miles
*Assistant Examiner* — Wade Miles
(74) *Attorney, Agent, or Firm* — Fish & Tsang

(57) ABSTRACT

A suturing instrument using a curved needle is presented. The suturing instrument includes an elongated body, which has a lumen at its distal end. The suturing device also includes a curved needle which has a hook at its distal end to capture a suture from a suture staging area coupled with the suture. The rotational movement of the curved needle can be operated by a linear movement of a controlling element via a compound pivots that are configured to move the needles out from the lumen, couple the needle to the suture, and pull the suture away back toward the lumen.

27 Claims, 6 Drawing Sheets

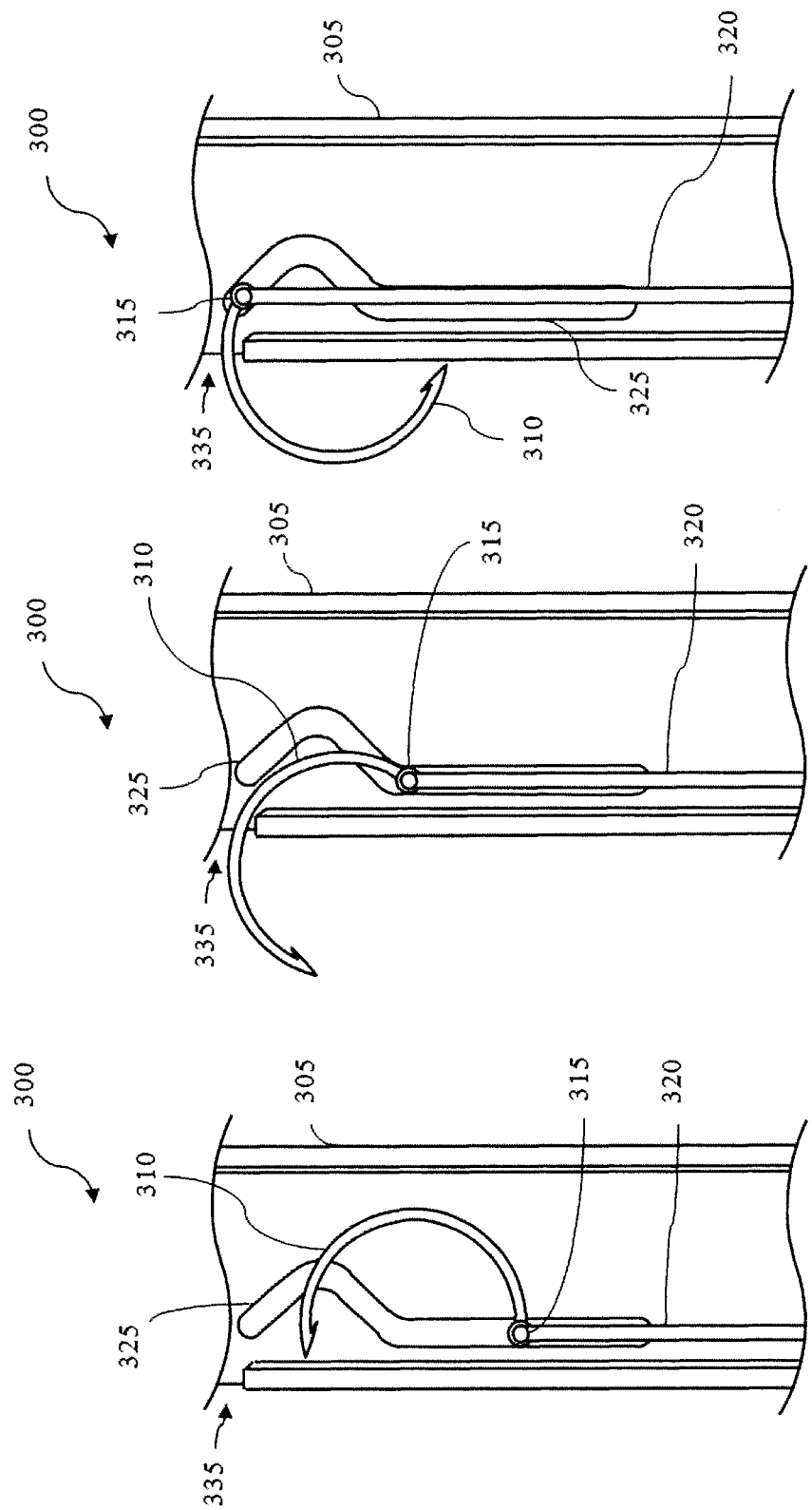

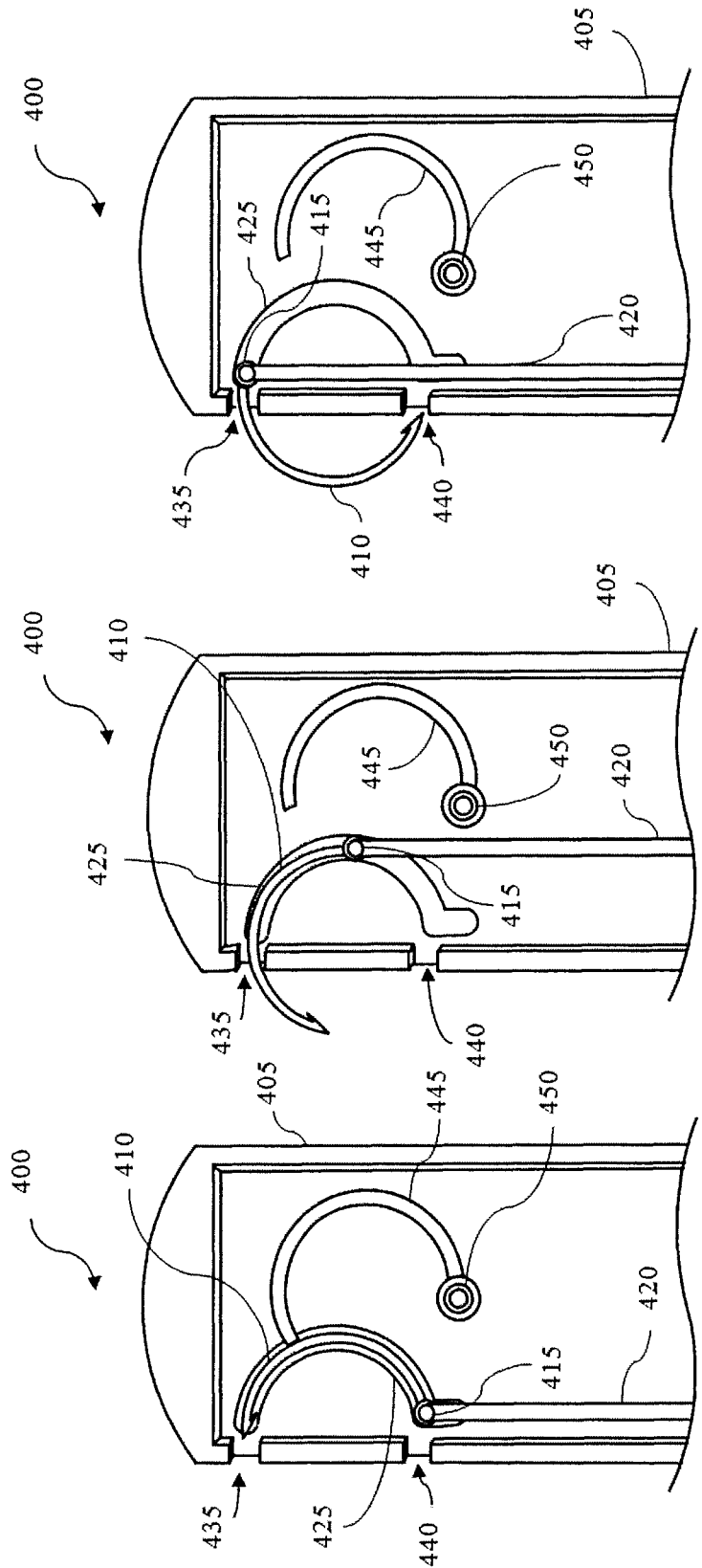

THROW AND CATCH SUTURING DEVICE WITH A CURVED NEEDLE

This application claims the benefit of priority to U.S. Provisional Patent Application No. 62/267,771, filed Dec. 15, 2015, which is incorporated by reference herein in its entirety.

FIELD OF THE INVENTION

The field of the invention is a suturing of tissue.

BACKGROUND

The background description includes information that may be useful in understanding the present invention. It is not an admission that any of the information provided herein is prior art or relevant to the presently claimed invention, or that any publication specifically or implicitly referenced is prior art.

Health practitioners frequently use sutures to close various cuts, punctures, incisions or other openings in various places in the human body. In many instances, sutures are convenient to use and function properly to hold openings in biological tissue closed, thereby aiding in blood clotting, healing, and prevention of scarring. Depending on types and sizes of tissues to be sutured, different types of needles, suture threads, and suture devices can be used in the suturing process. Yet, there appear to be no commercially available suture devices designed for "throw and catch" suturing, where a curved needle first passes through the tissue (the "throw"), and then picks up a suture thread (the "catch"). Still further, there appear to be no "throw and catch" suture devices that a physician can operate, through a catheter or trocar, to properly direct a suture needle along a curved path within the target tissue.

Engineers have developed various wheeled systems for directing curved needles along curved paths. For example, U.S. Pat. No. 5,709,693 to Taylor discloses a stitching device that incrementally advances an arc needle in a circular path. In Taylor, the needle is coupled to both a static clutch body and a dynamic clutch body. Linear movements of a shaft result operate the static clutch body, which then moves a drive plate. The drive plate rocks the dynamic clutch body, which incrementally advances the arc needle. Similarly, U.S. Pat. No. 8,123,764 to Meade discloses a suturing device, in which a suture needle rotates by movements of multiple wheels that is engaged with an actuator. Neither Taylor nor Meade, however, contemplate any "throw and catch" mechanism.

Others also have developed various guide systems for directing curved needles along curved paths. For example, in U.S. Pat. No. 6,346,111 to Gordon discloses a suturing device having a needle guide track. In Gordon, the needle guide track is deployed to the suture site by a linear movement of an actuator. The needle delivers the suture to the catch site, which is a "catch and throw" mechanism, rather than a "throw and catch" mechanism.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for improved endoscopic suture device that allows a suture that follows the natural curvature of the curved needle and operates through a throw-and-catch mechanism.

SUMMARY OF THE INVENTION

The inventive subject matter provides systems and methods for a throw-and-catch suturing, which directs a curved needle through tissue along a path that follows the needle's natural curvature, and that is operated by a linear movement of an actuator.

One aspect of the invention includes a suturing instrument having an elongated body with proximal and distal ends, a curved needle having a hook, and a suture staging area that cooperates with the needle to hook a suture. A compound pivot moves the needle out from a lumen in the distal end of the device, to where the hook hooks the suture, and then pulls the hook and suture away from the suture staging area and back into the lumen.

Another aspect of the invention includes a suturing instrument similar to that described above, but where a channel or other needle guide replaces the compound pivot.

Another aspect of the invention includes a method of suturing a tissue by providing a suture instrument as described above, advancing the curved needle through the tissue toward the suture staging area, coupling the hook to the suture, and then pulling the suture away from the suture staging area, and then back towards the lumen. In some embodiments, the suture staging area is moved by operating a first trigger, and the compound pivot is moved toward a first direction so that the needle moves out of the lumen distal end by operating a second trigger.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIGS. 3A-C illustrate one embodiment of a system to advance a curved needle.

FIGS. 4A-C illustrate another embodiment of a system to advance a curved needle.

DETAILED DESCRIPTION

Figure 1:
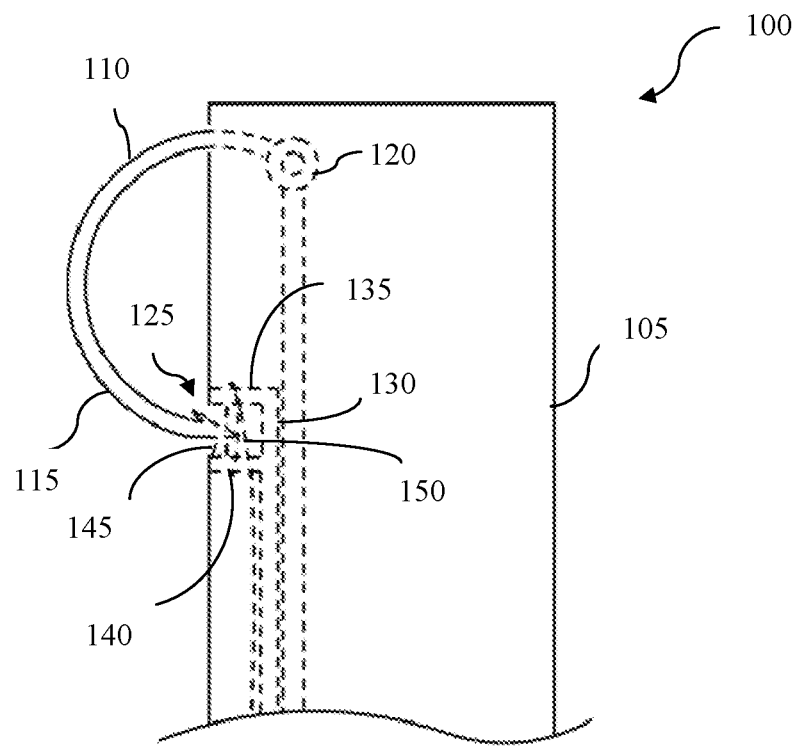
FIG. 1 illustrates a schematic of a suturing instrument having a curved needle and a suture staging area.

The inventive subject matter provides apparatus and systems of suturing instrument for a curved needle operated by a throw-and-catch mechanism and methods of suturing a tissue using a curved needle by throw-and-catch the curved needle.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities or ranges, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In one aspect of the inventive subject matter, a suturing instrument includes an elongated body that has a proximal end and a distal end. As used herein, the term "proximal end" refers to an end close to the user (e.g., a medical provider, a technician, etc.) and the term "distal end" refers to an end close to the patient. In preferred embodiments there is at least one lumen extending from proximal to distal ends, in which is disposed at least one wire that controls movement of the needle.

In FIG. 1, suturing instrument 100 includes an elongated body 105, a curved needle 110, and a suture staging area 130. The curved needle is coupled with the elongated body 105 via a pivot 120, which allows rotational movement of the curved needle 110 along an arc of at least 60 degrees, at least 90 degrees, at least 150 degrees, or at least 180 degrees, etc. Typically, the curved needle 110 has a shape subtending an arc of about 90°-225°. However, for use in small diameter catheters and trocars, the curved needle subtends a smaller arc, preferably 120°-180° and in some cases about 150°-180°.

Curved needle 110 includes a hook 115 at its distal end to facilitate catching a portion of a suture 150 via the hook 115. In a preferred embodiment, the hook 115 comprises a pointed end (e.g., a barb, an arrowed end, etc.) to puncture a part of a tissue to move forward to the suture staging area 130.

The curved needle can comprise any suitable types of material, but especially biocompatible materials. For example, the curved needle can comprise plastic materials (e.g., polypropylene, polyethylene, nylon, PVC or PTFE), metal materials (e.g., aluminum, copper, platinum, gold, metal alloys, etc.), or a glass fiber.

The suture staging area 130 is configured to hold and supply a portion of the suture 150 for "catching" by the curved needle 110. In one exemplary embodiment, the suture staging area 130 includes an upper arm 135 and a lower arm 140. A portion of the suture 150 is looped between the upper and the lower arms 135, 140. The upper arm and the lower arm are spaced sufficiently far apart (e.g., at least 1 mm, at least 5 mm, at least 10 mm, etc.) to accommodate of the catching of the suture 150 by the hook 115.

Additionally, the suture staging area 130 can include a suture cutter 145, which can cut the suture 150 as needed. The suture cutter 145 is preferably located at the outer end of the lower arm 140 or at the outer end of the upper arm 135, but could also be placed in any suitable location between the suture loop and the outer ends of the lower arm 140 or the upper arm 135.

Typically, the suture staging area 130 is located in the lumen of the distal end of the elongated body 105. In these embodiments, the elongated body 105 further includes a needle accepting area 125, through which a portion of the curved needle 110 can pass to access to the suture staging area 130. The needle accepting area 125 can be an opening on the wall of the distal end of the elongated body 105. In some embodiments, the opening is coupled with a closure (e.g., a door, a flap, a camera shutter-type leaves, etc.) to avoid constant exposure of the lumen of the elongated body 105 to the environment of the outside of the elongated body 105.

Figure 2:
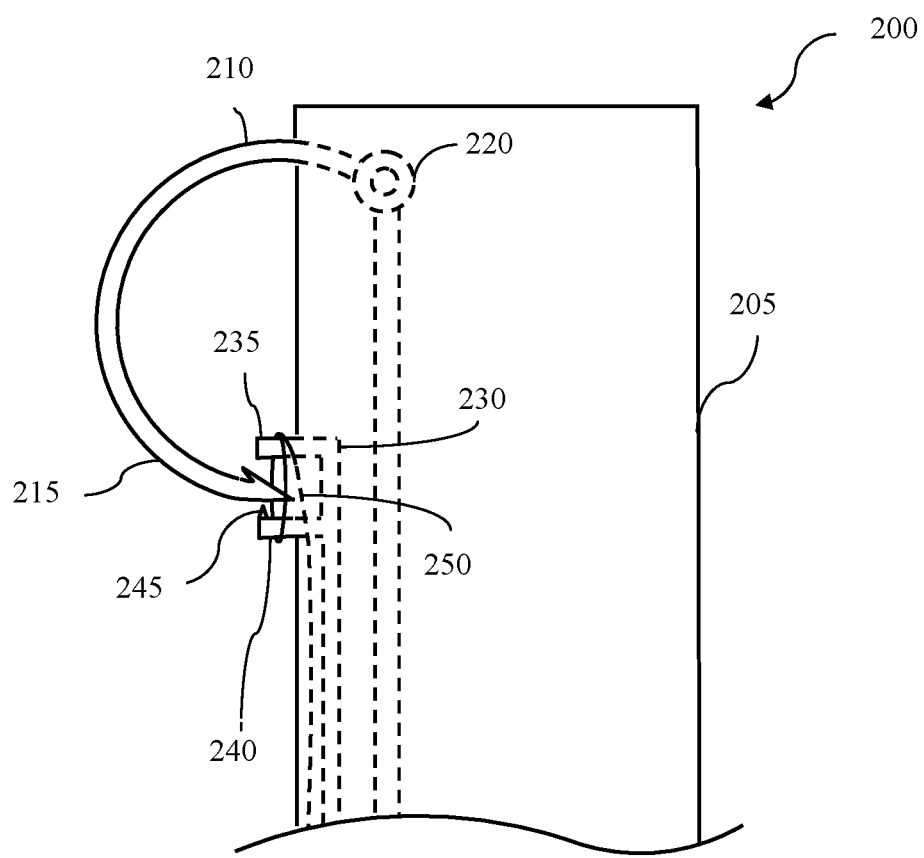
FIG. 2 illustrates a schematic of an alternative suturing instrument, having a curved needle and a suture staging area.

In FIG. 2, a suturing instrument 200 includes an elongated body 205, a curved needle 210, and a suture staging area 230 with a suture cutter 245. The curved needle is coupled with the elongated body 205 via a pivot 220, which allows rotational movement of the curved needle 210 along an arc of at least 60 degrees, at least 90 degrees, at least 150 degrees, or at least 180 degrees, etc. Typically, the curved needle 210 has a shape subtending an arc of about 90°-225°. However, for use in small diameter catheters and trocars, the curved needle subtends a smaller arc, preferably 120°-180° and in some cases about 150°-180°.

In this embodiment, at least a portion of the suture staging area 230 is exposed outside of the elongated body 205. Preferably, at least a portion of the upper arm 235 and the lower arm 240, around which a portion of the suture 250 is wrapped, are located outside of the elongated body 20, such that the hook 215 of the curved needle 210 can access to the suture loop without entering the elongated body 205. Additionally, in this embodiment, the elongated body 205 includes an opening through which the suture 250 can pass, so that only a portion of the suture 250 is exposed to the environment of the outside of the elongated body 205.

Advancing a curved needle through tissue, along a natural arc of the needle, requires rotational movement of the needle about a pivot. Such movement is difficult to effect using a needle that is positioned via a catheter or trocar. Also, it is beneficial to minimize the size (e.g., a width, a diameter) of the elongated body to allow easy access through small and narrow body areas (e.g., vascular structures), and thereby minimize the trauma experienced by patients. Thus, to reduce the size of the elongated body, it is desired for a suturing device to have a mechanism that translates a linear movement of an operating handle into a rotation movement of the curved needle. As used herein, the term a "linear movement" refers a linear movement along a length of the elongated body from the proximal end to the distal end.

In some embodiments, linear movement of an operator's handle can be translated to a rotation movement of a curved needle by coupling the needle with a pivot, and moving the pivot along a rail. FIGS. 3A-C show an exemplary embodiment 300 in which a curved needle 310 is coupled with an extension of operator's handle 320 via a pivot 315. The pivot 315 is configured to (or constrained to) move along rail 325, which is embossed on an inner surface of the elongated body 305. Rail 325 has three main sections, a substantially linear portion 325A, a centrally deviating portion 325B, and a laterally deviating portion 325C.

As shown in FIGS. 3A-B, when the handle 320 is linearly pushed toward the distal end of the elongated body 305, the pivot 315 and the curved needle 310 move straight toward the distal end of the elongated body 305 along the substantially linear portion 325A. As the pivot 315 moves along the centrally deviating portion 325B, the distal end of the curved needle 310 reaches needle dispatch opening 335, and makes a first rotational movement toward the outside of the elongated body 305.

As pivot 315 moves further along the centrally deviating portion 325B of rail 325 and then the laterally deviating portion 325C of the rail as shown in FIGS. 3B-C, the curved needle 310 rotates further outside of the elongated body 305, subtending an arc even greater than 180°. Thus, in this embodiment 300, a linear (e.g., straight from proximal to distal) movement of the handle 320 is translated into a curvilinear movement of the pivot 315 (straight and then curved movement along the rail), which in turn is translated into a rotational movement of the curved needle 310. Depending on the size and arc of the curved needle 310, the radius or diameter of lumen in which the curved needle 310 is initially disposed, the rail 325 can have many different shapes (e.g., a U-shape, a V-shape, etc.).

In FIGS. 4A-C, the curved needle 410 is again coupled with a linear handle 420 via a pivot 415, and the pivot 415 is configured to (or constrained to) move along a rail 425 embossed on an inner surface of the elongated body 405. However, in this embodiment, the rail 425 is shaped like an arc similar to the curved needle 410 (e.g., an arc of 120°-180°, etc). Additionally, the embodiment 400 includes a directing element 445 rotationally movable via an independent pivot 450. In some embodiments, the directing element and the independent pivot are coupled to a second handle (not shown) that is operated independently from the handle 420.

As shown in FIGS. 4A-B, when the handle 420 is linearly pushed toward the distal end of the elongated body 405, the pivot 415 and the curved needle 410 move straight toward the distal end of the elongated body 405 along the first portion of the rail 425 which is straight from the proximal to the distal end of the elongated body 405. When the pivot 415 reaches the point of the rail 425 where the rail is curved, the distal end of the curved needle 410 reaches an opening for needle dispatch 435 and make a first rotational movement toward the outside of the elongated body 405.

Then, as shown in FIGS. 4B-C, when the pivot 415 moves along the curved portion of the rail 425, the curved needle 410 makes a rotational movement about 180 degrees at the outside of the elongated body 405 toward a needle accepting area 440. In this embodiment 400, linear movement of the pivot along the rail 425 moves the pivot 415 first in a straight movement, and then in a curved movement. Those movements, in turn, produce rotational movement of the curved needle 410.

This particular embodiment includes a directing element 445, which is positioned to assist in directing the curved needle 410 to move along a desired path. Directing element 445 is a semicircular object, but all other objects that achieve a similar function are contemplated.

In some embodiments, a smooth, rotational movement of a curved needle can be achieved using compound pivots. As used herein, the term "compound pivot" means a linkage having multiple pivots, in which movement of one pivot affects movement of another pivot. Some contemplated embodiments include linkages compound pivot with 3, 4 or more pivots.

Figure 5C:
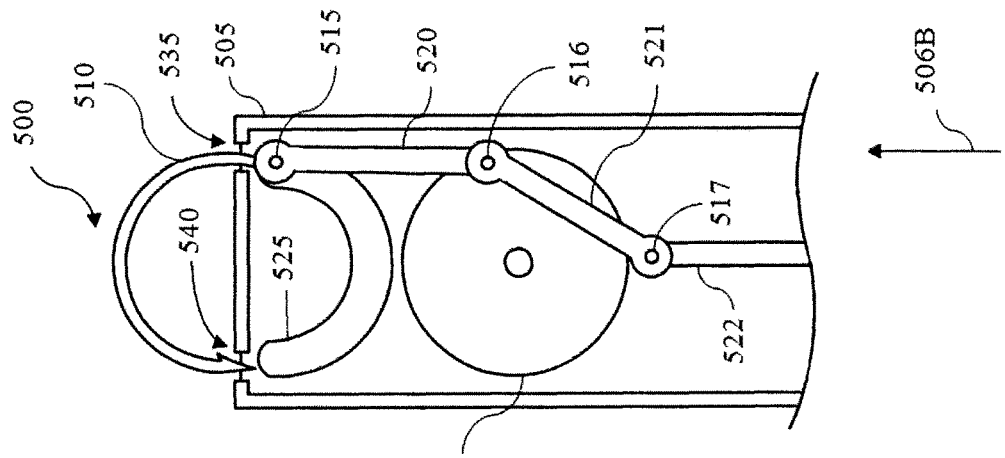
FIGS. 5A-C illustrate another embodiment of a system to advance a curved needle.
Figure 5B:
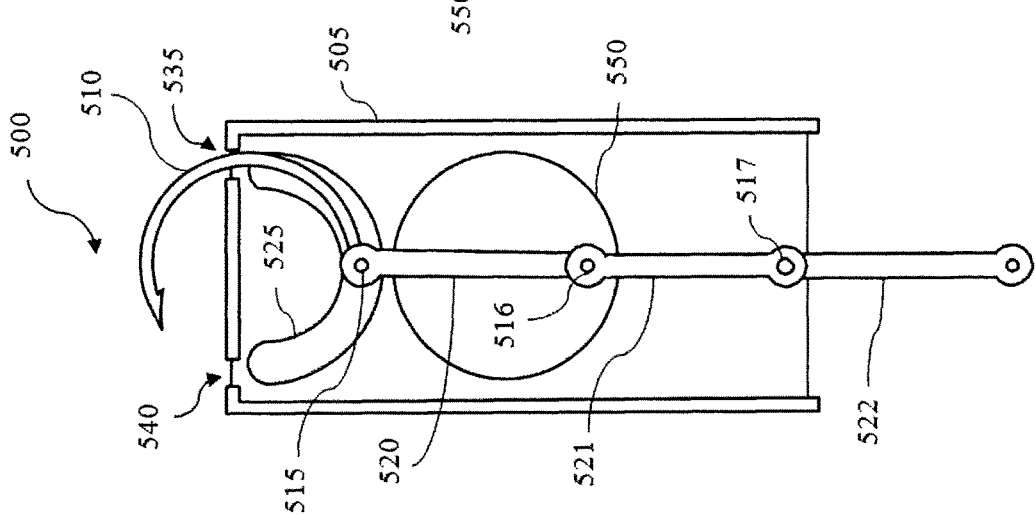
Figure 5A:
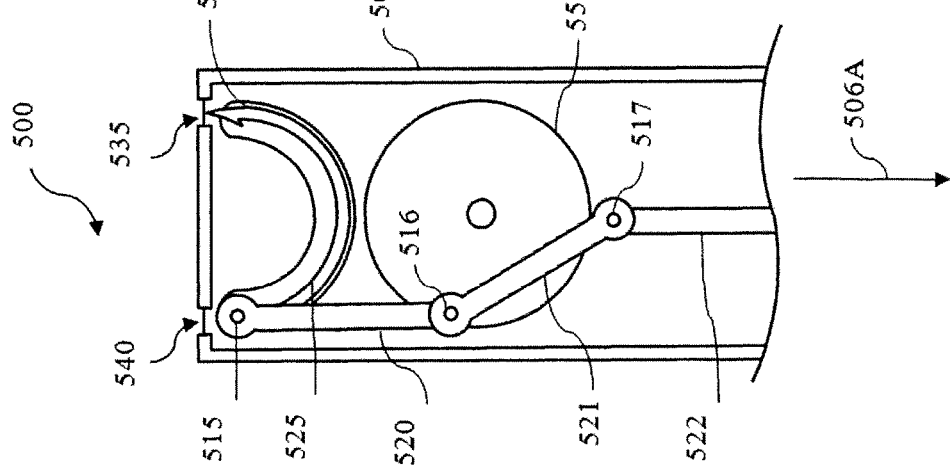

In FIGS. 5A-C, suture device 500 includes a curved needle 510 coupled with a linear handle (a controlling element) 522 via a plurality of linear elements 520, 521, and a plurality of pivots 515, 516, 517 mechanically coupling the curved needle with intermediate elements 520, 521. Specifically, the handle 522 is coupled with the first linear element 521 via the first pivot 517, and the first linear element 521 is coupled with the second linear element 520 via a second pivot 516. The second linear element 520 is coupled with the curved needle 510 via a third pivot 515.

In a preferred embodiment, the second pivot 516 is placed on a curved element 550 (e.g., a wheel, a half wheel, etc.) such that the linear movement of the handle 522 is translated to a circular (or semi-circular) movement of the second pivot 516 along the circumference (or a circle concentric with the circumference) of the curved element 550. In the particular embodiment shown, the third pivot 515 is placed on a curved path 525 (e.g., a needle guide), which has a similar arc angle with the curved needle 510, such that movement of the second pivot 516 along the circumference of the curved element 550 can be translated to the curved movement of the third pivot 515 and the curved needle 510.

In some embodiments, the curved path 525 is embossed on an inner surface of the lumen of the elongated body 505. In other embodiments, it is contemplated that the curved path 525 comprises a needle guide, which is made of resilient materials (e.g., a plastic material, a fibrous material, a rubber material) and placed on an inner surface of the lumen of the elongated body 505.

As shown in FIGS. 5A-B, when the handle 522 is pulled linearly toward the proximal end of the elongated body 505 (pulled away from the distal end of the elongated body 505, as shown by arrow 506A), the first pivot 517 is pulled away from the distal end of the elongated body 505. When the first pivot 517 is moved toward the proximal end of the elongated body 505, the second pivot 516 is also pulled away toward the proximal end of the elongated body 505 along the circumference of the curved element 550, which moves about 90 degrees counterclockwise. When the second pivot 516 is rotationally moved counterclockwise and toward the proximal end of the elongated body 505, the third pivot 515 moves along the curved path 525 about a half way such that the third pivot 515 is located most proximally at the curved path 525. As the third pivot 515 moves along the curved path 525, the curved needle 510 approaches the opening 535 for dispatching the needle and makes a first rotational movement toward the outside of the elongated body 505.

As shown in FIGS. 5B-C, when the handle 522 is linearly pushed toward the distal end of the elongated body 505, as shown by arrow 506B, the first pivot 517 is pushed toward the distal end of the elongated body 505. Then, the second pivot 516 is also pushed toward the distal end of the elongated body 505 along the circumference of the curved element 550 in a counterclockwise manner. When the second pivot 516 is rotationally moved counterclockwise and toward the distal end of the elongated body 505, the third pivot 515 moves along the curved path 525 about another half way such that the third pivot 515 is located most distally at the curved path 525. As the third pivot 515 moves along the curved path 525, the curved needle 510 further rotates (e.g., 180 degrees or more) toward the needle accepting area 540. In some embodiments, a suture staging area (not shown) is located inside of the needle accepting area 540, or at the needle accepting area 540, such that the needle can couple to the suture, and pull the suture away from the suture staging area (not shown) back to the opening 535 for dispatching the needle and the lumen of the elongated body 505.

Figure 6C:
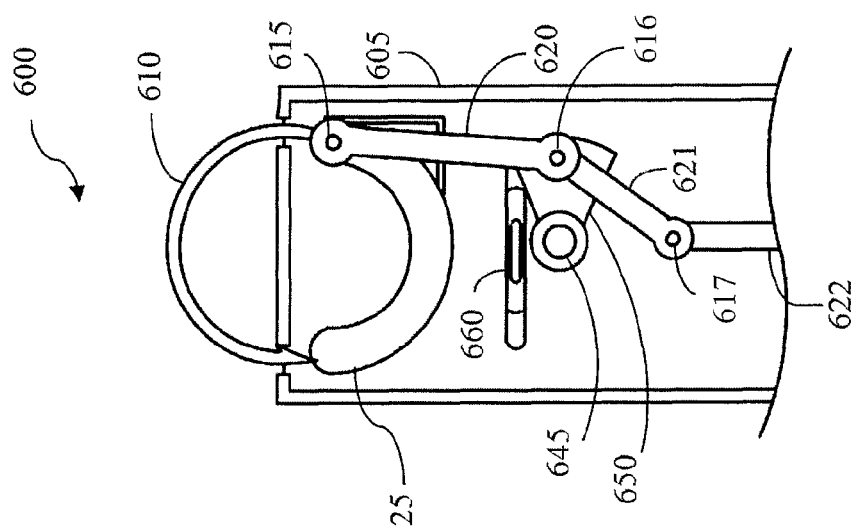
FIGS. 6A-C illustrate still another embodiment of a system to advance a curved needle.
Figure 6B:
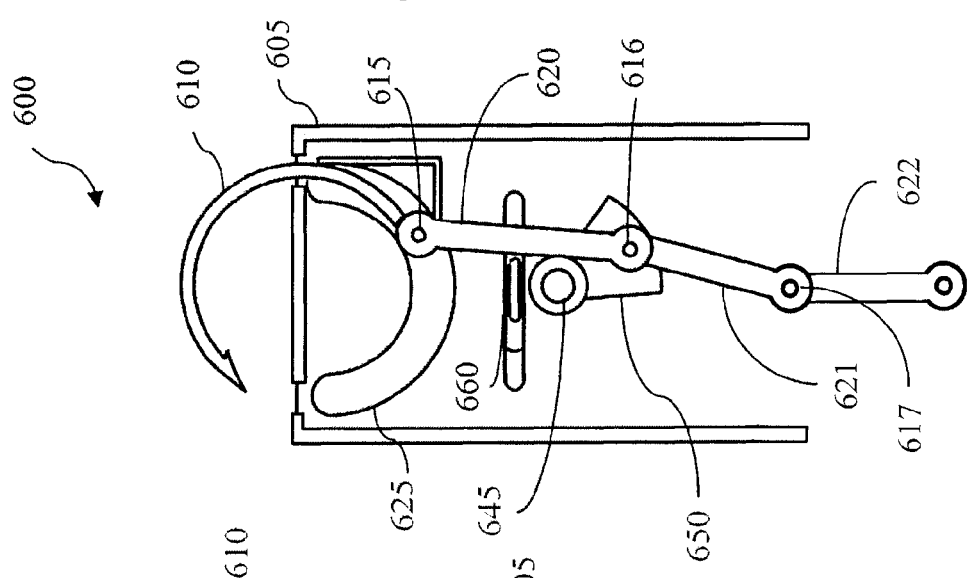
Figure 6A:
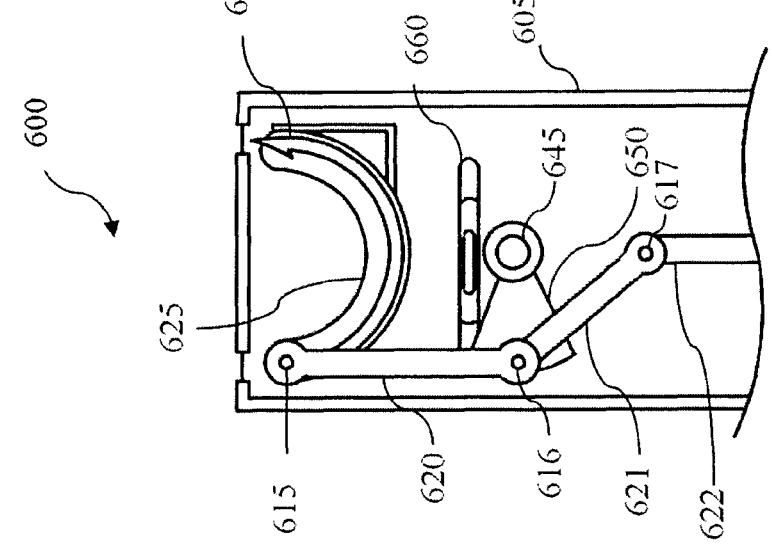

FIGS. 6A-C shows another exemplary embodiment 600 using compound pivots. In this embodiment 600, the curved needle 610 is coupled with a linear handle 622 via a plurality of linear elements 620, 621, and a plurality of pivots 615, 616, 567 connecting the curved needle and intermediate elements 620, 621. Again, the handle 622 is coupled with the first linear element 621 via the first pivot 617, the first linear element 621 is coupled with the second linear element 620 via a second pivot 616, and the second liner element 620 is coupled with the curved needle 610 via a third pivot 615.

In this embodiment, however, the second pivot 616 is placed on a sector-shaped (fan shaped) curved element 650 such that the linear movement of the handle 622 is translated to a rotational movement of the second pivot 616 with a rotational movement of the curved element 650. More preferably, the second pivot 616 is attached or affixed at the curved element 650 such that movement of either the curved element 650 or the second pivot 616 moves the second pivot 616 or the curved element 650, respectively. In this embodiment, the third pivot 615 is placed on a curved path 625 (e.g., a needle guide), which has a similar arc angle with the curved needle 610 such that the movement of the second pivot 616 with a rotational movement of the curved element 650 can be translated to the curved movement of the third pivot 615 and the curved needle 610.

As shown in FIGS. 6A-B, when the handle 622 is linearly pulled toward the proximal end of the elongated body 605 (pulled away from the distal end of the elongated body 605, as shown by arrow 606A), the first pivot 617 is pulled away from the distal end of the elongated body 605. When the first pivot 617 is moved toward the proximal end of the elongated body 605, the second pivot 616 is also pulled away toward the proximal end of the elongated body 605, which is accompanied with the rotational movement of the curved element 650, which moves about 90 degrees counterclockwise. When the second pivot 616 is rotationally moved counterclockwise and toward the proximal end of the elongated body 605, the third pivot 615 moves about half way along the curved path 625, such that the third pivot 615 is located most proximally at the curved path 625. As the third pivot 615 moves along the curved path 625, the curved needle 610 approaches the opening (not shown) for dispatching the needle and makes a first rotational movement toward the outside of the elongated body 605.

As shown in FIGS. 6B-C, when the handle 622 is linearly pushed toward the distal end of the elongated body 605, as shown by arrow 606B, the first pivot 617 is pushed toward the distal end of the elongated body 605. Then, the second pivot 616 is also pushed toward the distal end of the elongated body 605 accompanied with a rotational movement of the curved element 650 in a counterclockwise manner. When the second pivot 616 is rotationally moved counterclockwise and toward the distal end of the elongated body 605, the third pivot 615 moves along the curved path 625 about another half way such that the third pivot 615 is located most distally at the curved path 625. As the third pivot 615 moves along the curved path 625, the curved needle 610 further rotates (e.g., 180 degrees or more) toward the needle accepting area (not shown).

Optionally, the movement of the curved element 650 is limited by a stopper 660, which is located distally from the curved element 650. For example, when the curved element 650 is rotated leftward (clockwise), the stopper 660 prevents over-rotating of the curved element 650 (e.g., more than 90 degree, more than 120 degree, etc.). Similarly, when the curved element 650 is rotated rightward (counterclockwise), the stopper 660 prevents over-rotating of the curved element 650 (e.g., more than 90 degree, more than 120 degree, etc.). In some embodiments, the length or the location of the stopper is adjustable such that the movements of the curved element 650 are unevenly restricted based on the direction of movements (e.g., 90 degree movement in clockwise and 120 degree movement in counterclockwise, etc.).

In some embodiments, the suturing instrument also includes one or more triggers (not shown) that control movement of the suture staging area and/or compound pivots. For example, the suturing instrument can include a first trigger that is configured move the suture staging area in/out of the elongated body. In some other embodiments, the first trigger can be configured to open/close the closure covering the needle accepting area. For another example, the suturing instrument can include a second trigger that is configured to move the compound pivot toward a distal or proximal direction so that the needle moves out of the lumen of the elongated body. In some embodiments, the suturing instrument can further include a third trigger that is configured to move the compound pivot toward an opposite direction so that the needle moves back towards the lumen of the elongated body.

Another aspect of the invention includes a method of suturing a tissue using a curved needle. The method includes a step of providing a suturing instrument. The suturing instrument includes an elongated body having a proximal end and a distal end having a lumen, a curved needle having a hook, a suture disposed in a suture staging area, and a compound pivot (or a needle guide) disposed to move the needle out from the lumen. As used herein, a step of providing includes a step of supplying, selling, or placing the device.

Once the suturing instrument is provided, the method continues with a step of advancing the curved needle through the tissue toward the suture staging area. When the curved needle approaches the suture staging area, the method continues with a step of coupling the needle to the suture through a hook at the distal end of the needle. Then the method continues with a step of pulling the suture away from the suture staging area, and then back towards the lumen. Preferably, steps of advancing the needle and pulling the suture can be operated by a linear movement of a controlling element (e.g., a handle, etc.) that is configured to move linearly along a length of the elongated body. In some embodiments, one or both of (a) the linear movement of the controlling element and (b) a movement of the suture staging area can be achieved by operating one or more triggers coupled with the suturing instrument.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A suturing instrument, comprising:
   an elongated body having a lumen, a proximal end and a distal end;
   a curved needle having a hook;
   a suture disposed in a suture staging area;
   a compound pivot disposed to move the needle out from the lumen, couple the hook to the suture, and pull the suture away from the suture staging area, and then back towards the lumen; and
   wherein the compound pivot comprises a first pivot that is configured to translate toward the distal end within a rail positioned on a surface of the lumen.

2. The instrument of claim 1, wherein the suture staging area is disposed within the lumen.

3. The instrument of claim 1, wherein the hook is disposed in a distal end of a curved needle.

4. The instrument of claim 1, wherein the hook comprises a barb.

5. The instrument of claim 1, further comprising a needle accepting area, and wherein a portion of the suture staging area is exposed to the hook via the needle accepting area.

6. The instrument of claim 1, wherein the compound pivot comprises a first pivot and a second pivot, and the first pivot is disposed on a curved element.

7. The instrument of claim 1, wherein the compound pivot comprises a first pivot and a second pivot, and the first pivot is disposed on a linear element constrained to a curved path.

8. The instrument of claim 1, wherein the compound pivot comprises a second pivot that is configured to move along the rail from the proximal end to the distal end.

9. The instrument of claim 8, wherein the rail comprises a first path and a second path, the first and second paths are not parallel with each other such that movement of the compound pivots allows the curved needle to advance according to a needle's natural curvature.

10. The instrument of claim 1, wherein the compound pivot is coupled with a controlling element that is configured to move linearly along a length of the elongated body.

11. The instrument of claim 1, wherein the needle is in a semicircle shape.

12. The instrument of claim 1, wherein the compound pivot is configured to move the needle through an arc of at least 180 degrees.

13. The instrument of claim 1, further comprises first and second triggers, wherein the first trigger is configured to move the suture staging area and the second trigger is configured to move the compound pivot toward a first direction so that the needle moves out of the lumen toward the suture staging area.

14. The instrument of claim 13, further comprising a third trigger configured to move the compound pivot toward a second direction so that the needle moves back towards the lumen away from the suture staging area.

15. A method of suturing a tissue, comprising steps of:
   providing a suturing instrument, comprising:
      an elongated body having a proximal end and a distal end having a lumen;
      a curved needle having a hook;
      a suture disposed in a suture staging area;
      a compound pivot disposed to move the needle out from the lumen, wherein the compound pivot comprising a first pivot that is configured to translate towards the distal end within a rail positioned on a surface of the lumen;
   advancing the curved needle through the tissue toward the suture staging area;
   coupling the hook to the suture; and
   pulling the suture away from the suture staging area, and then moving back towards the lumen.

16. The method of claim 15, wherein the suture staging area is disposed within the lumen.

17. The method of claim 15, wherein the hook is disposed in a distal end of a curved needle.

18. The method of claim 15, wherein the hook comprises a barb and a point.

19. The method of claim 15, wherein the instrument further comprises a needle accepting area, and wherein a portion of the suture staging area is exposed to the hook via the needle accepting area.

20. The method of claim 15, wherein the compound pivot comprises a first pivot and a second pivot, and the first pivot is disposed on a curved element.

21. The method of claim 15, wherein the compound pivot comprises a first pivot and a second pivot, and the first pivot is disposed on a linear element constrained to a curved path.

22. The method of claim 15, wherein the rail comprises a first path and a second path, the first and second paths are not parallel with each other.

23. The method of claim 15, further comprising a step of linearly moving a controlling element that is configured to move linearly along a length of the elongated body.

24. The method of claim 15, wherein the needle is in a semicircle shape.

25. The method of claim 15, wherein the compound pivot is configured to move the needle through an arc of at least 180 degrees.

26. The method of claim 15, further comprising steps of:
   operating a first trigger to move the suture staging area;
   operating a second trigger to move the compound pivot toward a first direction so that the needle moves out of the lumen distal end.

27. The instrument of claim 26, further comprising a step of operating a third trigger to move the compound pivot toward a second direction so that the needle moves back toward the lumen.

* * * * *